United States Patent [19]

Moorehead et al.

[11] Patent Number: 4,800,194

[45] Date of Patent: Jan. 24, 1989

[54] ACYLPHOSPHOROTRIAMIDES USEFUL AS LIPID-ALTERING AGENTS

[75] Inventors: Thomas J. Moorehead; Allan V. Bayless, both of Norwich, N.Y.

[73] Assignee: Norwich Eaton Pharmaceuticals, Inc., Norwich, N.Y.

[21] Appl. No.: 938,195

[22] Filed: Dec. 5, 1986

Related U.S. Application Data

[62] Division of Ser. No. 761,992, Aug. 1, 1985, Pat. No. 4,668,667.

[51] Int. Cl.$^4$ .................. A61K 31/675; A61K 31/66; A61K 31/05; A61K 31/015
[52] U.S. Cl. ..................................... 514/89; 514/91; 514/112; 514/120; 514/138; 514/277; 546/22; 564/14
[58] Field of Search ................... 514/89, 91, 112, 120, 514/138, 177; 564/14; 546/22

[56] References Cited

U.S. PATENT DOCUMENTS

4,182,881 1/1980 Bayless et al. ..................... 546/22
4,221,730 9/1980 Alaimo et al. ............... 260/397.7 R
4,454,126 6/1984 Yamatsu et al. .................. 514/138

OTHER PUBLICATIONS

Kutty, K. M., R. Redheendran & D. Murphy, "Serum Cholinesterase: Function in Lipoprotein Metabolism", *Experentia*, vol. 33 (1977), pp. 420–422.
Kutty, K. M., R. Jain, S.-N. Huang & K. Kean, "Serum Pseudocholinesterase: High Density Lipoprotein Cholesterol Ratio as an Index of Risk for Cardiovascular Disease", *Clinica Chimica Acta*, vol. 115 (1981), pp. 55–61.
Jain, R., K. M. Kutty, S.-N. Huang & K. Kean, "Pseudocholinesterase/High-Density Lipoprotein Cholesterol Ratio in Serum of Normal Persons and of Hyperlipoproteinemics", *Clinical Chemistry*, vol. 29 (1983), pp. 1031–1033.
Cucuianu, M., T. A. Popescu & S. Haragus, "Pseudocholinesterase in Obese and Hyperlipemic Subjects", *Clinica Chimica Acta*, vol. 22 (1968), pp. 151–155.
Cucuianu, M., T. A. Popescu, A. Opincaru & S. Haragus, "Serum Pseudocholinesterase and Ceruloplasmin in Various Types of Hyperlipoproteinemia", *Clinica Chimica Acta*, vol. 59 (1975), pp. 19–27.
Cucuianu, M., A. Opincaru & D. Tapalaga, "Similar Behavior of Lecithin: Cholesterol Acyltransferase and Pseudocholinesterase in Liver Disease and Hyperlipoproteinemia", *Clinica Chimica Acta*, vol. 85 (1978), pp. 73–79.
Cucuianu, M. P., A. Cristea, S. Roman & I. Missits, "Increased Plasma Antithrombin III Level in Hyperlipidemic Subjects", *Clinica Chimica Acta*, vol. 110 (1981), pp. 147–155.
Ando, M., S. Hirosaki, K. Tamura & T. Taya, "Multiple Regression Analysis of the Cholinesterase Activity with Certain Physiochemical Factors", *Environmental Research*, vol. 33 (1984) pp. 96–105.
Kutty, K. M., J. D. Jacob, C. J. Hutton, P. J. Davis & S. C. Peterson, "Serum Beta-Lipoproteins: Studies of a Patient and in Guinea Pigs After the Ingestion of Organophosphorus Compounds", *Clinical Biochemistry*, vol. 8 (1975), pp. 379–383.
Kutty, K. M., "Review: Biological Function of Cholinesterase", *Clinical Biochemistry*, vol. 13 (1980), pp. 239–243.

*Primary Examiner*—John W. Rollins
*Attorney, Agent, or Firm*—Milton B. Graff, IV; Jack D. Schaeffer; David L. Suter

[57] ABSTRACT

The present invention involves compounds of the class of acylphosphorotriamides and methods for altering the blood plasma lipid content of mammals which comprises systemically administering to mammals an effective but nontoxic amount of a composition comprising such compounds.

10 Claims, No Drawings

ACYLPHOSPHOROTRIAMIDES USEFUL AS LIPID-ALTERING AGENTS

This is a division of application Ser. No. 761,992, filed on Aug. 1, 1985, now U.S. Pat. No. 4,668,667.

TECHNICAL FIELD

The present invention relates to compounds and compositions which are useful as blood plasma lipid-altering agents, and to the treatment of a host to alter the lipid content of the blood plasma of the host.

BACKGROUND OF THE INVENTION

It has been generally established that hyperlipidemia (high levels of lipids in blood plasma) is associated with several health related disfunctions such as atherosclerosis, diabetes, and obesity. Blood cholesterol levels have been particularly implicated in the incidence of atherosclerosis. More particularly, a high risk of cardiovascular disease has been shown to correlate with the ratio of low density lipoprotein (LDL) cholesterol to high density lipoprotein (HDL) cholesterol. Agents which can reduce the ratio of LDL/HDL have been shown to effectively lower the incidence of cardiovascular disease associated with atherosclerosis. While it is preferable to reduce the LDL/HDL ratio by reducing the level of LDL in blood plasma, reduction of the LDL/HDL ratio without significantly reducing the level of LDL has also been shown to correlate with lower risk of cardiovascular disease.

More recently, it has been shown that there is a relationship between blood levels of the enzyme pseudocholinesterase and hyperlipidemia. The possible treatment of hyperlipidemia by inhibition of blood plasma pseudocholinesterase is suggested by Kutty, K. M., R. Redheendran & D. Murphy, "Serum Cholinesterase: Function in Lipoprotein Metabolism", *Experientia*, Vol. 33 (1977), pp. 420-422. A study published in Kutty, K. M., R. Jain, S.-N. Huang & K. Kean, "Serum Pseudocholinesterase: High Density Lipoprotein Cholesterol Ratio as an Index of Risk for Cardiovascular Disease", *Clinica Chimica Acta*, Vol. 115 (1981), pp. 55-61, indicates that there is a significant increase in the ratio of plasma pseudocholinesterase/HDL cholesterol in subjects classified as high risk for cardiovascular disease on the basis of the ratio of total cholesterol/HDL cholesterol. The results of this study of 290 subjects suggest that plasma pseudocholinesterase has a parallel relationship with LDL and a reciprocal relationship with HDL. Further studies reported in Jain, R., K. M. Kutty, S.-N. Huang & K. Kean, "Pseudocholinesterase/High-Density Lipoprotein Cholesterol Ratio in Serum of Normal Persons and of Hyperlipoproteinemics", *Clinical Chemistry*, Vol. 29 (1983), pp. 1031-1033, show that the ratio of plasma pseudocholinesterase/HDL cholesterol is particularly high in subjects with certain types of hyperlipidemia. Similar results showing a correlation between high blood levels of pseudocholinesterase and hyperlipidemia are disclosed in Cucuianu, M., T. A. Popescu & S. Jaragus, "Pseudocholinesterase in Obese and Hyperlipemic Subjects", Clinica *Chimica Acta*, Vol. 22 (1968), pp. 151-155; Cucuianu, M., T. A. Popescu, A. Opincaru & S. Haragus, "Serum Pseudocholinesterase and Ceruloplasmin in Various Types of Hyperlipoproteinemia", *Clinica Chimica Acta*, Vol. 59 (1975), pp. 19-27; Cucuianu, M., A. Opincaru & D. Tapalaga, "Similar Behavior of Lecithin:Cholesterol Acyltransferase and Pseudocholinesterase in Liver Disease and Hyperlipoproteinemia", *Clinica Chimica Acta*, Vol. 85 (1978), pp. 73-79; and Cucuianu, M. P., A. Cristea, S. Roman & I. Missits, "Increased Plasma Antithrombin 111 Level in Hyperlipidemic Subjects", *Clinica Chimica Acta*, Vol. 110 (1981), pp. 147-155. A study reported in Ando, M., S. Hirosaki, K. Tamura & T. Taya, "Multiple Regression Analysis of the Cholinesterase Activity with Certain Physiochemical Factors", *Environmental Research*, Vol. 33 (1984), pp. 96-105, shows a significant positive correlation between blood plasma pseudocholinesterase levels and serum total cholesterol content.

Animal studies have shown that agents which inhibit cholinesterase activity will significantly decrease plasma LDL and/or significantly increase plasma HDL levels as reported in Kutty, Redheendran & Murphy, and in Kutty, K. M., J. D. Jacob, C. J. Hutton, P. J. Davis & S. C. Peterson, "Serum Beta-Lipoproteins: Studies of a Patient and in Guinea Pigs After the Ingestion of Organophosphorus Compounds", *Clinical Biochemistry*, Vol. 8 (1975), pp. 379-383. In Kutty, Jacob, Hutton, Davis & Peterson, it is reported that in a patient accidentally poisoned with parathione, a cholinesterase inhibitor, the blood plasma levels of pseudocholinesterase and LDL were markedly decreased and HDL was increased.

The physiological role of pseudocholinesterase has not been clearly established but in Kutty, K. M., "Review: Biological Function of Cholinesterase", *Clinical Biochemistry*, Vol. 13 (1980), pp. 239-243, evidence is presented that the enzyme is involved with lipid metabolism.

Several types of organophosphorus compounds are known to have cholinesterase inhibiting characteristics. Although they would likely be effective at lowering blood plasma levels of pseudocholinesterase, they are highly toxic because they also inhibit acetylcholinesterase, an enzyme involved in neuro transmission.

Certain acylphosphorotriamides are known, and it has been disclosed that some of these compounds have activity as inhibitors of the enzyme urease and therefore are useful in the treatment of certain urinary tract infections. U.S. Pat. Nos. 4,182,881 issued to Bayless & Millner on Jan. 8, 1980, and 4,221,730 issued to Alaimo, Storrin & Millner on Sept. 9, 1980, disclose certain acylphosphorotriamides and methods of synthesizing them and are hereby incorporated by reference.

SUMMARY OF THE INVENTION

It is an object of the present invention to provide a method of altering blood plasma lipid content in mammals.

It is a further object of the present invention to lower the ratio of low density lipoprotein cholesterol/high density lipoprotein cholesterol in the blood plasma of mammals.

It is also an object of this invention to provide novel compounds which alter the blood plasma lipid plasma content of mammals.

It is also an object of this invention to provide pharmaceutical compositions which alter the blood plasma lipid content of mammals.

The present invention provides a method for altering the blood plasma lipid content of a mammal which comprises systemically administering to such mammal an effective but nontoxic amount of a composition comprising a compound conforming to the following chemical structure:

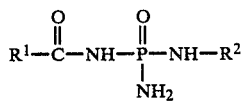

wherein
R² is H or straight or branched chain lower alkyl and R¹ is aryl or aralkyl;
and salts and/or hydrates thereof.

DETAILED DESCRIPTION OF THE INVENTION

In one of its aspects, the present invention is a method for altering the blood plasma lipid content of mammals which comprises systemically administering to such mammals an effective but nontoxic amount of a composition comprising certain acylphosphorotriamides as lipid-altering agents. The acylphosphorotriamides found to be useful as lipid-altering agents conform to the following chemical structure:

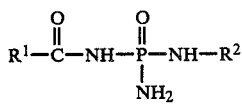

wherein
R² is H or straight or branched chain lower alkyl and R¹ is aryl or aralkyl;
and salts and/or hydrates thereof (Compounds A).

Preferred acylphosphorotriamides useful in the present invention include compounds which conform to the chemical structure of Compounds A hereinabove, but wherein R¹ is phenyl or substituted phenyl, pyridyl or substituted pyridyl, furyl or substituted furyl, naphthyl or substituted naphthyl, benzyl or substituted benzyl, or phenyl(lower) alkyl or substituted phenyl(lower) alkyl. More preferred are such compounds wherein R¹ is phenyl or substituted phenyl, furyl, or pyridyl. Still more preferred are such compounds wherein R¹ is 2-furyl, 3-pyridyl, phenyl, or 4-substituted phenyl wherein said phenyl substituent is selected from the group consisting of halo, lower straight or branched chain alkyl, lower straight or branched chain alkoxy, amino, nitro, lower straight or branched chain alkylsulfonyl, cyano, phenoxy or substituted phenoxy. Especially preferred are such compounds wherein R¹ is phenyl, 4-methoxyphenyl, 4-fluorophenyl, 3-fluorophenyl, 2-fluorophenyl, 4-methylphenyl, or 4-aminophenyl.

Preferred acylphosphorotriamides useful in the present invention include compounds which conform to the chemical structure of Compounds A hereinabove, but wherein R² is H.

Compounds which are useful in the present invention are potent irreversible inhibitors of pseudocholinesterase which exhibit minimal inhibition of acetylcholinesterase at the same concentration. The following method was used to determine the relative inhibition of pseudocholinesterase and acetylcholinesterase by compounds of the present invention.

TEST METHOD 1

Plasma (Source of Pseudocholinesterase Enzyme)

Human Plasma was obtained from blood which was collected in ethylenediaminetetraacetic acid (EDTA) treated tubes. Collected plasma was stored frozen at −20° C. until use.

Lysed Red Blood Cells (RBC's) (Source of Acetylcholinesterase Enzyme)

Human blood which was collected in EDTA treated tubes was centrifuged at 1500×g for 10 min. at 4° C. One volume of chilled 0.9% saline solution was gently mixed with one volume of packed RBC's. One volume of this suspension was then washed three times with ten volumes of chilled 0.9% saline solution (4° C.). Each wash was centrifuged at 1500×g for 10 min. at 4° C. and supernatant was discarded. After the last wash the supernatant was replaced with deionized, distilled water (treated by Milli-Q apparatus, Millipore Corp., Bedford, MA) (4° C.). After 15 min. at 4° C. the suspension was centrifuged at 1500×g for 10 min. at 4° C. The supernatant (lysed RBC's) was stored frozen at −20° C. until use.

Buffer/Chromogen

The buffer/chromogen solution was 0.25 mM 5,5'-dithiobis-[2-nitrobenzoic acid] (chromogen), 50 mM phosphate buffer, pH 7.2. In making up the buffer/chromogen solution and to keep it as colorless as possible, the phosphate buffer was first adjusted to pH 7.1 with NaOH; the chromogen was then added and dissolved; the pH was adjusted to 7.2; and the final volume was adjusted with addition of Milli-Q water. 5,5'-dithiobis-(2-nitrobenzoic acid) was obtained from Sigma Chemicals, St. Louis, MO.

Substrate

The substrate solution for the pseudocholinesterase assay was 156 mM S-butyrylthiocholine iodide, and the substrate solution for the acetylcholinesterase assay was 156 mM S-acetylthiocholine iodide. Both substrate compounds were obtained from Sigma Chemicals.

Test Compound Stock Solutions

Solutions of all test compounds were made up at 2 μM, 20 μM, and 200 μM concentrations (in 0.9% saline solution) except as noted where lower concentrations were necessary because of decreased solubility of the compound in saline solution.

Procedure

Pseudocholinesterase (PChE) Assay

In three separate tubes, a 100 μl aliquot of either 0.9% saline solution, 2 μM test compound solution, or 20 μM test compound solution was mixed with a 100 μl aliquot of human plasma, and the tubes were placed in a 35° C. water bath. Four cuvettes, each containing 3 ml buffer/chromogen solution mixed with 100 μl substrate solution (156 mM S-butyrylthiocholine iodide), had been placed in a heated cuvette holder (35° C.) in a Beckman DU-8B Spectrophotometer (Beckman Instruments). After the temperature of the buffer/chromogen/substrate solution in the cuvette had equilibrated for about 10 minutes, and after 0 or 30 minutes incubation of the plasma/test compound solution, a 25 μl aliquot of the plasma/test compound solutions was added to the corresponding cuvettes numbered 2–4. Cuvette #1 remained a blank. After mixing, the net absorbance of each cuvette was determined at 405 nm every 35 seconds for ten readings. From a plot of net absorbance versus time, the initial linear portion of the curve was determined, and a rate of absorbance change per minute was calculated. The positive control (100% PChE activity) was the plasma/saline solution.

Acetylcholinesterase (AChE) Assay

The acetylcholinesterase assay was performed identically to the pseudocholinesterase assay with the following exceptions. The concentrations of the stock solutions of test compounds were 20 μM and 200 μM, instead of 2 μM and 20 μM, and the substrate solution was 156 mM S-acetylthiocholine iodide instead of S-butyrylthiocholine iodide. The lysed RBC's/test compound solution was incubated for 0 and 60 minutes instead of 0 and 30 minutes before being added to the cuvette containing the buffer/chromogen/substrate solution. From a plot of net absorbance versus time there was an initial period before the curve reached a steady linear rate. From this linear portion of the curve a rate of absorbance change per minute was calculated.

Results

Each compound was tested for its ability to inhibit plasma pseudocholinesterase activity and acetylcholinesterase activity. Because of variation in the time points in the linear portion of the curve, inhibition values below 10–15% and higher than 85–90% are nearly indistinguishable from 0% and 100%, respectively. The values exhibited after 30 minutes of preincubation of enzyme with test compound is considered the irreversible % PChE inhibition; for % AChE inhibition, the values exhibited after 60 minutes of preincubation of enzyme are used.

EXAMPLES 1–28

Test compounds having the following chemical structure were tested for pseudocholinesterase and acetylcholinesterase inhibition according to the above test method.

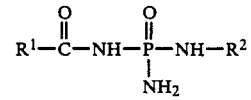

The results of the tests are provided in Table 1:

TABLE 1

| Test Compound | $R^1$ | $R^2$ | % PChE Inhibition 1 μM | % PChE Inhibition 10 μM | % AChE Inhibition 10 μM | % AChE Inhibition 100 μM |
|---|---|---|---|---|---|---|
| 1 | -phenyl | —H | 92.7 | 99.1 | 4.1 | 37.3 |
| 2 | -3-pyridyl | —H | 84.1 | 97.6 | −1.9 | 70.7 |
| 3 | -4-nitrophenyl | —H | 90.4 | 99.0 | 64.3 | 86.9 |
| 4 | -4-fluorophenyl | —H | 92.8 | 99.1 | 12.4 | 52.3 |
| 5 | -4-aminophenyl | —H | 57.7 | 98.2 | 1.8 | 32.1 |
| 6 | -4-chlorophenyl | —H | 87.7 | 98.7 | 5.4 | 86.5 |
| 7 | -3-nitrophenyl | —H | 65.6 | 98.9 | 23.9 | 86.6 |
| 8 | -4-methoxyphenyl | —H | 83.4 | 96.3 | 3.0 | 34.2 |
| 9 | -4-methylphenyl | —H | 73.7 | 98.1 | 9.6 | 46.0 |
| 10 | -2-methylphenyl | —H | 21.4 | 89.2 | 8.6 | 44.5 |
| 11 | -2-chlorophenyl | —H | 49.5 | 98.5 | 32.1 | 87.3 |
| 12 | -4-cyanophenyl | —H | 97.4 | 98.8 | 34.4 | 85.5 |
| 13 | -3-fluorophenyl | —H | 80.2 | 98.8 | −4.0 | 41.3 |
| 14 | -3-trifluoromethylphenyl | —H— | 25.0 | 94.1 | 25.7 | 85.9 |
| 15 | -2-fluorophenyl | —H | 97.4 | 99.3 | 14.7 | 82.1 |
| 16 | -4-(1,1-dimethylethyl)phenyl | —H | 46.3 | 97.9 | 3.1 | 38.7 |
| 17 | -2-napthyl | —H | 27.4[a] | 95.1[a] | 16.0[a] | 87.2[a] |
| 18 | -benzyl | —H | 10.7 | 61.3 | 17.1 | 85.2 |
| 19 | -3-phenoxyphenyl | —H | 63.7 | 98.3 | 15.8 | 64.2 |
| 20 | -4-(methylsulfonyl)phenyl | —H | 92.9 | 98.5 | 20.5 | 86.4 |
| 21 | -2,6-difluorophenyl | —H | 74.4 | 98.7 | 51.1 | 93.7 |
| 22 | -4-butoxyphenyl | —H | 28.8 | 94.9 | 12.6 | 57.4 |
| 23 | -phenylethenyl | —H | 11.5 | 73.2 | 6.6 | 54.8 |
| 24 | -4-biphenyl | —H | 5.3[b] | 66.6[b] | −3.7[b] | 34.8[b] |
| 25 | -3-[[(4-aminophenyl)sulfonyl]amino]phenyl | —H | 97.2 | 99.0 | 62.2 | 88.5 |
| 26 | -2-furyl | —H | 91.0 | 98.7 | 7.7 | 73.0 |
| 27 | -4-fluorophenyl | -isopropyl | 8.7[c] | 43.3[c] | 5.8[c] | 32.2 [c] |
| 28 | -5-nitro-2-furyl | —H | 21.0 | 90.8 | 46.9 | 93.1 |

[a]0.5 μM and 5.0 μM for PChE and 5 μM and 50 μM for AChE
[b]0.25 μM and 2.5 μM for PChE and 2.5 μM and 25 μM for AChE
[c]10 μM and 100 μM for PChE and 50 μM and 500 μM for AChE All 28 of the test compounds showed substantially greater inhibition of pseudocholinesterase than acetylcholinesterase.

The above results show that compounds of the present invention, at certain concentrations, have the ability to strongly inhibit pseudocholinesterase while having only a minimal inhibitory effect on acetylcholinesterase.

The activity of compounds of the present invention in reducing the ratio of LDL/HDL in hyperlipidemic guinea pigs is demonstrated by the following example:

TEST METHOD 2 AND EXAMPLE 29

Guinea Pigs

Male Hartley guinea pigs (Elm Hill Breeding Labs., Chelmsford, MA or Charles River, Wilmington, MA) was used in all experiments unless otherwise specified. The animals were maintained on a normal diet of rabbit pellets (Purina Rabbit Chow 5321, Ralston Purina, St. Louis, MO) and water containing 0.1% ascorbic acid ad libitum. For special studies in the hyperlipidemic guinea pig model, the animals were maintained on the high cholesterol diet described in this report and water containing 0.1% ascorbic acid ad libitum.

Individual animals were identified by ear and cage markings. The dose of drug or placebo was adjusted daily for changes in the weight of the guinea pigs. Blood samples were collected in EDTA Vacutainers by open chest cardiac puncture under carbon dioxide anesthesia from guinea pigs which had been fasted overnight. The animals were then sacrificed by $CO_2$ inhalation. Blood samples were centrifuged at 2000 rpm for 15 min. in an IEC centrifuge (International Equipment Co., Boston, MA) with a 240 rotor for isolation of plasma. Lipoprotein analyses of plasma were carried out on the same day as the blood collection. Assays of pseudocholinesterase activity were carried out within a week of blood collection on plasma samples which had been stored at 4° C.

Pseudocholinesterase Assay

The assay method used was based on the procedure described in Ellman, G. L., K. D. Courtney, V. Andres & R. M. Featherstone, "A New and Rapid Colorimetric Determination of Acetylcholinesterase Activity", *Biochemical Pharmacology*, Vol. 7 (1961), pp. 88–95. Reactions were carried out at 35° C. in pH 7.2 $NaH_2PO_4$ 50 mM buffer containing 5 mM butyrylthiocholine iodide (substrate) and 0.25 mM 5,5'-dithiobis-[2-nitrobenzoic acid] (chromogen). The rate of change of absorbance at 405 nm with time was monitored by means of a Cary 16 spectrophotometer (Varian Associates, Walnut Creek, CA) or a Beckman DU-8B spectrophotometer (Beckman Instruments, Inc., Palo Alto, CA). Corrections were made for non-enzymic hydrolysis of substrate.

Reagents

Enzyme Buffer: 6.90 g (50 mmol) $NaH_2PO_4 \cdot H_2O$ + 0.9914 g (0.25 mmol) 5,5'-dithiobis-(2-nitrobenzoic acid). The reagents were dissolved in Milli-Q purified distilled water, titrated to pH 7.2 with 1N NaOH, and diluted to one liter with water.

Substrate: 0.2476 g (0.780 mmol) S-butyrylthiocholine iodide (BTC). The substrate was dissolved in 5 ml of Milli-Q purified distilled water. [BTC] = 156 mM.

Procedure (Cary 16 Spectrophotometer)

Into a 1-cm pathlength cuvette was placed 3.0 ml of enzyme buffer. At least 10 min. was allowed for temperature equilibration. A 100 μl aliquot of substrate was added to the cuvette, the solution was mixed and about 3 min. was allowed for determination of the non-enzymic rate of substrate hydrolysis before the enzymic reaction was initiated by addition of 25 μl of plasma. The increase in absorbance at 405 nm was measured vs. a blank containing enzyme buffer.

Procedure (Beckman DU-8B Spectrophotometer)

Into a 1-cm pathlength cuvette was placed 3.0 ml of enzyme buffer and 100 μl of substrate. The solution was mixed and about 10 min. was allowed for temperature equilibration. The reaction was initiated by addition of 25 μl of plasma. The increase in absorbance at 405 nm was measured vs. a blank containing enzyme buffer and substrate. No additional correction for non-enzymic substrate hydrolysis was necessary.

Lipoprotein Analysis

Freshly prepared samples of EDTA plasma were analyzed for lipoproteins with the Redi-Disc Lipoprotein Electrophoresis Kit (Miles Laboratories, Elkhart, IN) by the procedure recommended in the package insert supplied in the kit.

Reagents (Stored at 4° C.)

Redi-Disc Lipoprotein Gel Tubes, polyacrylamide 3%, buffer, preservative.

Redi-Disc Lipoprotein Loading Gel, acrylamide 2.5 g/dl., N,N'-methylenebisacrylamide 0.6 g/dl, sudan black B 13 mg/dl, catalyst, stabilizer, buffer.

Redi-Disc Lipoprotein Buffer, Trishydroxymethylaminomethane 27% w/w, boric acid 73% w/w, pH of solution 7.4–7.9 (11 g diluted to 1200 ml with water).

Procedure

The gel tubes were removed from the storage buffer and shaken to remove excess buffer. A 25 μl aliquot of plasma was added to each tube and mixed with 200 μl of loading gel. The loading gel was photopolymerized for 30–40 min. under a fluorescent light. The gel tubes were placed in the electrophoresis apparatus (Buchler Instruments, Fort Lee, NJ) and Redi-Disc Liproprotein Buffer was then added to the upper and lower chambers of the apparatus. The current was adjusted to 5 mA per gel tube. Electrophoresis was stopped when the HDL band was about 4–5 mm from the bottom of the gel tube.

The gels were stored in water for at least 30 min. following electrophoresis to allow the lipoprotein zones to spread. The gels were scanned at 615 nm in either a Beckman Acta C111 spectrophotometer or a Beckman DU-8B spectrophotometer. The areas of the lipoprotein peaks (VLDL, LDL, and HDL) were determined by gravimetric analysis (cut and weighed) on the Acta C111 or by electronic integration on the DU-8B.

High Cholesterol Diet

A 1:15 mixture of cholesterol:corn oil was prepared by adding 25 g of USP cholesterol (Sigma Chemical Company, St. Louis, MO) to 375 g of corn oil (Mazola, Best Foods, CPC International, Inc., Englewood Cliffs, NJ). The mixture was stirred, sonicated, and heated in a hot water bath until the cholesterol completely dissolved. It was necessary to keep the mixture warm (50°–60° C.) in order to prevent congealing.

Batches of feed were prepared by adding 160 g of the cholesterol-corn oil solution to 840 g of Purina Rabbit Chow 5321. The pellets and lipid mixture were thoroughly mixed in a 2-liter or 3-liter Erlenmeyer flask to ensure uniform coating of the pellets. The feed was then stored at room temperature until needed.

Hyperlipidemia Induced by Cholesterol Feeding

A control group of five male Hartley guinea pigs was maintained on a normal diet of Purina Rabbit Chow 5321 and water containing 0.1% ascorbic acid. A second group of five male guinea pigs was given the high-cholesterol diet described in this report and water containing 0.1% ascorbic acid. After seven days on the respective diet, the animals were fasted overnight and allowed only water containing 0.1% ascorbic acid. The animals were anesthetized by $CO_2$ inhalation and blood was collected by open chest cardiac puncture into EDTA Vacutainers. Then the animals were sacrificed by $CO_2$ inhalation. Plasma was separated and analyzed for lipoproteins by electrophoresis and assayed for pseudocholinesterase activity.

Multiple Dose Studies (Hyperlipidemic Guinea Pigs)

Two groups of male Hartley Guinea pigs were maintained on the high cholesterol diet described above and water containing 0.1% ascorbic acid ad libitum. One group was treated once daily with a freshly prepared solution of test compound 4, N-(diaminophosphinyl)-4-fluorobenzamide, (1.0 mg/ml in 0.9% saline solution) at 2.5 mg/kg by intraperitoneal injection for 14 days. The second group was given 0.9% saline solution once daily at 2.5 ml/kg by intraperitoneal injection for 14 days. Blood samples were collected in EDTA Vacutainers by open chest cardiac puncture under carbon dioxide anesthesia from guinea pigs which had been fasted overnight. Blood samples were obtained from selected control (saline treated) animals before treatment on days 0, 1, 3, 7, 10, and 14, and from selected dosed (test compound 4) animals before treatment on days 1, 3, 7, 10, and 14. The animals were sacrified by $CO_2$ inhalation after blood collection. Plasma was isolated by centrifugation and analyzed for lipoprotein and for pseudocholinesterase activity.

Results

Hyperlipidemia Induced by Cholesterol Feeding

The LDL/HDL ratio of the cholesterol-fed guinea pigs, 4.36, was significantly ($p<0.05$) greater than that of the normally fed guinea pigs, 1.98. The levels of pseudocholinesterase were not affected by the cholesterol feeding, 5500 and 5550 nmol/min/ml., respectively, for the two groups of guinea pigs.

Multiple Dose Studies (Hyperlipidemic Guinea Pigs)

Guinea pigs maintained on a high cholesterol diet and treated once daily with test compound 4 at 2.5 mg/kg i.p. had substantially lower plasma pseudocholinesterase activity than did saline-treated control animals. On the 14th day of treatment the LDL/HDL ratio was significantly lower ($p<0.05$) for the test compound 4-treated animals compared to that for control animals given the same diet but given daily injections of saline. The results are summarized in Table 2:

TABLE 2

Multiple Dose Studies (Hyperlipidemic Guinea Pigs)

| Day | % PChE Inhibition (Test Compound 4 Compared to Control) | LDL/HDL Test Compound 4 | LDL/HDL Control |
|---|---|---|---|
| 1 | 51.6 | 1.91 | 2.45 |
| 3 | 45.0 | 2.43 | 2.28 |
| 7 | 58.6 | 4.08 | 4.25 |
| 10 | 65.0 | 2.75 | 3.23 |
| 14 | 69.0 | 1.50[a] | 2.60 |

[a]Significantly different from Control value ($p < 0.05$).

Another aspect of the present invention is certain acylphosphorotriamides which are novel compounds and are useful as lipid-altering agents.

Novel compounds of the present invention include compounds of the class of acylphosphorotriamides which conform to the chemical structure of Compounds A except for such acylphosphorotriamides which are disclosed in Bayless & Millner incorporated by reference hereinabove.

Novel compounds of the present invention include compounds of the class of acylphosphorotriamides which conform to the chemical structure of Compounds A, except such compounds wherein $R^2$ is H and $R^1$ is 3-pyridyl, 2-furyl, 2-naphthyl, cinnamenyl, benzyl, phenyl, or phenyl substituted by 3- or 4-nitro, 4-halo, 4-amino, 4-(lower)alkoxy, 4-(lower)alkyl, 2-methyl, 2,3-dimethyl, 2,4-dimethyl, 2,4,6-trimethyl, 3-trifluoromethyl, 3-[(4-aminophenyl)sulfonyl]amino, 4-cyano, 4-phenyl, or 3-phenoxy (Compounds B).

Preferred novel compounds of the present invention include Compounds B, wherein $R^1$ is phenyl or substituted phenyl, pyridyl or substituted pyridyl, furyl or substituted furyl, naphthyl or substituted naphthyl, benzyl or substituted benzyl, or phenyl(lower)alkyl or substituted phenyl(lower)alkyl. More preferred compounds of the present invention include Compounds B wherein $R^1$ is phenyl or substituted phenyl, furyl, or pyridyl. More preferred still novel compounds of the present invention include Compounds B wherein $R^1$ is 2-furyl, 3-pyridyl, phenyl, or 4-substituted phenyl wherein said phenyl substituents are selected from the group consisting of halo, lower straight or branched chain alkyl, lower straight or branched chain alkoxy, amino, nitro, lower straight or branched chain alkylsulphonyl, cyano, phenoxy or substituted phenoxy. Especially preferred novel compounds of the present invention include Compounds B wherein $R^1$ is phenyl, 4-methoxyphenyl, 3-fluorophenyl, 2-fluorophenyl, 4-fluorophenyl, 4-methylphenyl, or 4-aminophenyl.

Preferred novel compounds of the present invention include Compounds B, wherein $R^2$ is H.

Methods for preparing novel compounds of the present invention are generally analagous to the methods of preparing acylphosphorotriamides disclosed in U.S. Pat. Nos. 4,182,881 and 4,221,730 which have been incorporated herein by reference. Further examples of methods for preparing novel compounds of the present invention are the following:

EXAMPLE 30

Test compound 20 above, N-(diaminophosphinyl)-4-(methylsulfonyl)benzamide, was prepared by the following method.

To a suspension of 5.04 g (0.025 mole) of p-methylsulfonylbenzamide in 50 ml of $CHCl_3$ was added 5.27 g (0.025 mole) of phosphorus pentachloride. The reaction was refluxed for 18 min., and was filtered to give 1.27 g of starting material.

To the filtrate was added .89 g of 97% formic acid. (This is 0.019 mole, which takes into account the starting material recovered.) Much gas was evolved (CO and HCl) and a precipitate formed. After 1 hr. of stirring at room temperature, the reaction was filtered to give a white solid.

This was suspended in 50 ml of tetrahydrofuran and was stirred in an ice bath for 1¼ hr. while $NH_3$ was blown in. The reaction was filtered, and the residue was washed with water to afford 4.4 g (84%) of white solid, m.p. 245°-260° (some unmelted at 300° C.).

Recrystallization from DMF gave 2.55 g of shiny, white platelets, m.p. 236°-22310° C.

Anal. Calcd. for $C_8H_{12}N_3O_4PS$: C, 34.66; H, 4.36; N, 15.16. Found: C, 34.22; H, 4.38; N, 15.34.

EXAMPLE 31

Test compound 27 above, N-[amino-(1-methylethylamino)phosphinyl]-4-fluorobenzamide, was prepared using the following method.

A mixture of 4-fluorobenzamide (9.98 g, 0.0717 mol) phosphorous pentachloride (14.98 g, 0.0719 mol, Aldrich Chemical Co.) and carbon tetrachloride (100 ml, A.R.) was stirred and heated at 60°-70° C. for ½ hour. Cooling to 25°-30° C. and adding formic acid (95-97%, 2.8 ml, 0.074 mol) dropwise while keeping the termperature below 10° C. gave a white precipitate. Collecting and rinsing the solid with chloroform gave 15.15 g (83% yield) of acid chloride. The acid chloride (15.15 g, 0.0592 mol was stirred in chloroform (100 ml, A.R.) and 90% of the theoretically required isopropylamine (9 ml, 6.2 g, 0.1057 mol) was added dropwise, keeping the temperature below 10° C. The reaction was allowed to warm to room temperature while stirring for 3 hours. This solution was added to an ammonia-saturated solution of chloroform (200 ml. A.R.) over a 1½ hour time period and stirring was continued overnight. Filtering gave 9 g consisting of a mixture of by-products. The chloroform filtrate was washed with water (6×200 ml) and the aqueous layer then salted with sodium chloride and extracted with chloroform (8×225 ml). Combining the chloroform layers, drying over magnesium sulfate, and concentrating the filtrate gave 0.570 g (4%) of N-[amino-(1-methylethylamino)phosphinyl]-4-fluorobenzamide; m.p. 197°–199° C.

Anal. Calcd. for $CH_{10}H_{15}FN_3O_2P$: C, 46.34; H, 5.83; N, 16.21. Found: C, 46.20; H, 6.05; N, 15.92.

Another aspect of the present invention is a composition in dosage unit form for altering plasma lipids of mammals comprising an effective but nontoxic amount of the novel acylphosphorotriamides having lipid-altering activity disclosed hereinabove. The composition is preferably adapted to systemic administration to mammals.

As used herein, the term "pharmaceutical carrier" denotes a solid or liquid filler, diluent, or encapsulating substance. Some examples of the substances which can serve as pharmaceutical carriers are sugars, such as lactose, glucose and sucrose; starches, such as corn starch and potato starch; cellulose and its derivatives, such as sodium carboxymethylcellulose, ethylcellulose and cellulose acetate; powdered tragacanth; malt, gelatin; talc, stearic acid; magnesium stearate; calcium sulphate; vegetable oils, such as peanut oil, cottonseed oil, sesame oil, olive oil, corn oil, and oil of thiobroma; polyols, such as propylene glycol, glycerine, sorbitol, mannitol, and polyethylene glycol; agar; alginic acid; pyrogen-free water; isotonic salines; and phosphate buffer solutions; as well as other nontoxic compatible substances used in pharmaceutical formulations. Wetting agents and lubricants, such as sodium lauryl sulphate, as well as coloring agents, flavoring agents and preservatives, can also be present.

The pharmaceutical carrier employed in conjunction with the lipid-altering acylphosphorotriamides is used at a concentration sufficient to provide a practical size-to-dosage relationship. Preferably, the pharmaceutical carrier comprises from about 0.1% to about 99% by weight of the total composition.

Preferred dosage unit forms the compositions of the present invention include capsules, tablets, solutions and suspensions to be administered orally and solutions and suspensions to be administered perenterally. Preferred dosage unit forms include solutions and suspensions to be administered perenterally comprising from about 2 mg to about 1000 mg of a novel lipid-altering acylphosphorotriamide and a suitable pharmaceutical carrier; more preferred is such a dosage unit form comprising from about 5 mg to about 250 mg of such compound; more preferred still is such a dosage unit form comprising from about 10 mg to about 50 mg of such compound. Other preferred dosage unit forms includes capsules and tablets each comprising from about 2 mg to about to about 1000 mg of a novel lipid-altering acylphosphorotriamide and a suitable pharmaceutical carrier; more preferred is such a dosage unit form comprising from about 5 mg to about 250 mg of such compound; more preferred still is such a dosage unit form comprising from about 10 mg to about 50 mg of such compound.

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A compound of the class of acylphosphorotriamides which conform to the chemical structure:

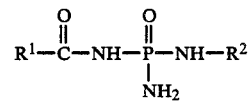

wherein $R^2$ is H or straight or branched chain lower alkyl and $R^1$ is substituted phenyl, pyridyl or substituted pyridyl, furyl or substituted furyl, naphthyl or substituted naphthyl, benzyl or substituted benzyl, or phenyl(lower)alkyl or substituted phenyl(lower) alkyl; except such compounds wherein $R^2$ is H and $R^1$ is 3-pyridyl or 2-furyl or 2-naphthyl or cinnamenyl or benzyl or phenyl substituted by 3-nitro or 4-nitro or 4-halo or 4-amino or 4-(lower)alkoxy or 4-(lower)alkyl or 2-methyl or 2,3-dimethyl or 2,4-dimethyl or 2,4,6-trimethyl or 3-trifluoromethyl or 3-((4-aminophenyl)-sulfanyl)amino or 4-cyano or 4-phenyl or 3-phenoxy.

2. The compound of claim 1 wherein $R^2$ is H.

3. The compound of claim 2 wherein $R^1$ is 4-substituted phenyl wherein said phenyl substituents are selected from the group consisting of lower straight or branched chain alkylsulfonyl, phenoxy and substituted phenoxy.

4. The compound of claim 2 wherein $R^1$ is 3-fluorophenyl.

5. The compound of claim 2 wherein $R^1$ is 2-fluorophenyl.

6. A composition in dosage unit form for altering the blood plasma lipid content of a mammal comprising: (1) an effective but nontoxic amount of the compound of claim 1, and (2) a pharmaceutical carrier.

7. A composition in dosage unit form for altering the blood plasma lipid content of a mammal comprising: (1) an effective but nontoxic amount of the compound of claim 2, and (2) a pharmaceutical carrier.

8. A composition in dosage unit form for altering the blood plasma lipid content of a mammal comprising: (1) an effective but nontoxic amount of the compound of claim 3, and (2) a pharmaceutical carrier.

9. A composition in dosage unit form for altering the blood plasma lipid content of a mammal comprising: (1) an effective but nontoxic amount of the compound of claim 4, and (2) a pharmaceutical carrier.

10. A composition in dosage unit form for altering the blood plasma lipid content of a mammal comprising: (1) an effective but nontoxic amount of the compound of claim 5, and (2) a pharmaceutical carrier.

* * * * *